United States Patent
Ando et al.

(10) Patent No.: US 11,066,635 B2
(45) Date of Patent: Jul. 20, 2021

(54) METHOD OF CULTURING CELLS

(71) Applicant: Panasonic Corporation, Osaka (JP)

(72) Inventors: Takeshi Ando, Kyoto (JP); Toshiaki Yamauchi, Kyoto (JP); Norihiro Shibata, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 16/189,328

(22) Filed: Nov. 13, 2018

(65) Prior Publication Data

US 2019/0078048 A1 Mar. 14, 2019

Related U.S. Application Data

(63) Continuation of application No. 15/327,648, filed as application No. PCT/JP2015/004488 on Sep. 4, 2015, now abandoned.

(30) Foreign Application Priority Data

Dec. 19, 2014 (JP) .............................. JP2014-257357

(51) Int. Cl.
| | |
|---|---|
| *C12M 1/34* | (2006.01) |
| *C12M 1/00* | (2006.01) |
| *G06T 7/00* | (2017.01) |
| *G02B 21/36* | (2006.01) |
| *G06T 7/60* | (2017.01) |

(52) U.S. Cl.
CPC ........... *C12M 41/46* (2013.01); *C12M 41/36* (2013.01); *C12M 99/00* (2013.01); *G02B 21/365* (2013.01); *G06T 7/0012* (2013.01); *G06T 7/60* (2013.01); *G06T 2207/10056* (2013.01); *G06T 2207/30024* (2013.01)

(58) Field of Classification Search
CPC ...... C12M 41/46; C12M 41/36; C12M 99/00; G02B 21/365
See application file for complete search history.

(56) References Cited

U.S. PATENT DOCUMENTS

2009/0035857 A1* 2/2009 Chesnut ................. C12M 33/18
435/396
2013/0038727 A1* 2/2013 Clark ..................... C12M 41/48
348/143

FOREIGN PATENT DOCUMENTS

| JP | 2003-116530 | 4/2003 |
| JP | 2010-099011 | 5/2010 |

OTHER PUBLICATIONS

Jaccard et al. "Automated Method for the Rapid and Precise Estimation of Adherent Cell Culture Characteristics from Phase Contrast Microscopy Images" (2014) Biotech & Bioengineer, vol. 111: 504-517 (Year: 2014).*
International Search Report of PCT application No. PCT/JP2015/004488 dated Dec. 8, 2015.

* cited by examiner

*Primary Examiner* — Teresa E Knight
(74) *Attorney, Agent, or Firm* — Panasonic IP Management; Kerry S. Culpepper

(57) ABSTRACT

A method of culturing cells including: dividing a culture area into a center area and a plurality of peripheral areas, and designating the center area and the plurality of peripheral areas as measurement positions; calculating: a confluent rate at each of the measurement positions designated; and an average confluent rate which is an average of sum of the confluent rates at the measurement positions designated, the confluent rate being defined as a proportion of an area occupied by cells in a designated area; and determining a timing to perform a subculture of the cells, based on the confluent rate, wherein the determining of the timing further includes determining when the average confluent rate is smaller than a first threshold value, the confluent rate of the center area is larger than a second threshold value, and the second threshold value is larger than the first threshold value.

7 Claims, 5 Drawing Sheets

METHOD OF CULTURING CELLS

TECHNICAL FIELD

The present invention relates to a method of culturing cells that automatically determines a subculture timing.

BACKGROUND ART

In a culture of cells, since the cells are spread over an entire culture vessel through cell proliferation, a subculture operation needs to be performed every few days. In a technology in the related art, image processing is performed on a cell observation image by a microscope or the like, and thereby a proportion of an area in the observation image, which is occupied by cells, is calculated. The subculture is performed at a timing at which the proportion exceeds a predetermined threshold value (for example, see PTL 1).

In addition, there is a cell culture apparatus in which cells at a plurality of positions in the culture vessel are observed, and which causes the culture vessel to oscillate in consideration of variations (for example, see PTL 2).

CITATION LIST

Patent Literature

PTL 1: Japanese Patent Unexamined Publication No. 2003-116530

PTL 2: Japanese Patent Unexamined Publication No. 2010-99011

SUMMARY OF THE INVENTION

The present invention provides a method of culturing cells in which it is possible to determine an appropriate subculture timing, based on image information.

A method of culturing cells including:
dividing a culture area into a center area and a plurality of peripheral areas, and designating the center area and the plurality of peripheral areas as measurement positions;
calculating:
a confluent rate at each of the measurement positions designated; and
an average confluent rate which is an average of sum of the confluent rates at the measurement positions designated, the confluent rate being defined as a proportion of an area occupied by cells in a designated area; and
determining a timing to perform a subculture of the cells, based on the confluent rate,
wherein the determining of the timing further includes determining when the average confluent rate is smaller than a first threshold value, the confluent rate of the center area is larger than a second threshold value, and the second threshold value is larger than the first threshold value.

According to the present invention, it is possible to determine an appropriate subculture timing.

DESCRIPTION OF EMBODIMENT

Before an exemplary embodiment of the present invention is described, a problem of a cell culture apparatus in the related art is briefly described.

In a case of determining a subculture timing as in PTL 1, a state of an entire culture vessel is estimated from an observation image taken at one position; however, the cells rarely grow evenly in the vessel during a cell culture, and thus there is a possibility that it is difficult to determine the subculture timing with accuracy.

In addition, in a case where an operation of the cell culture apparatus is determined, based on the measurement at a plurality of positions of the culture vessel as in PTL 2, the easiness of distribution of the cells in the culture vessel is not considered and thus there is a possibility that a difference will be found in a result of the measurement at positions through a selected method.

Hereinafter, the exemplary embodiment of the present invention will be described with reference to the accompanying figures.

Note that the same components are assigned with the same reference signs and thus description thereof is omitted in some cases.

In addition, the figures schematically illustrate the components as main bodies for easy understanding.

Figure 1:
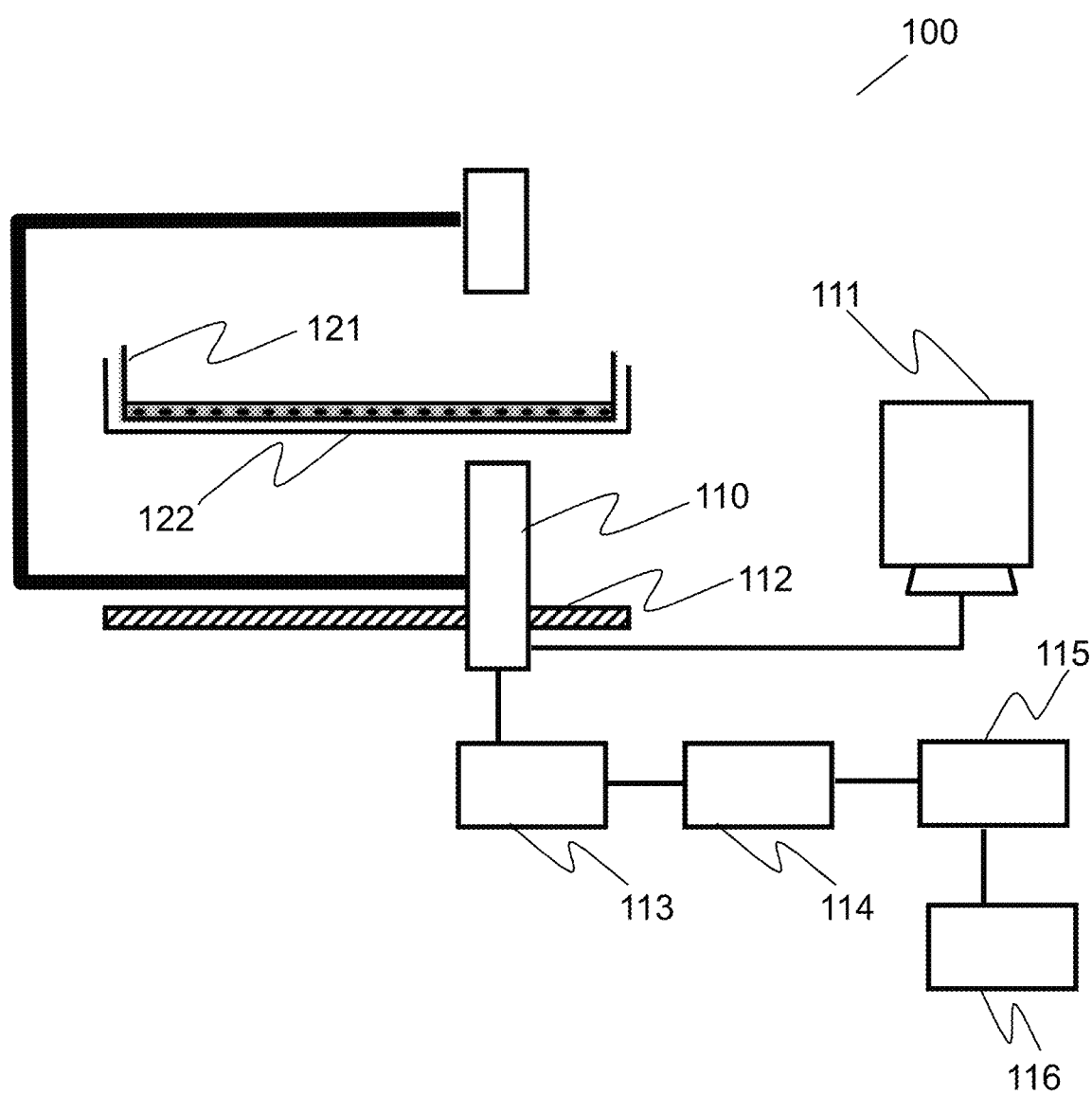
FIG. 1 is a schematic diagram illustrating a cell culture apparatus according to an exemplary embodiment of the present invention.

FIG. 1 is a schematic diagram illustrating cell culture apparatus 100 according to the exemplary embodiment of the present invention.

Cell culture apparatus 100 calculates a confluent rate in a plurality of measurement positions in culture vessel 121, and thereby it is possible to perform a subculture at the optimum timing in consideration of uneven spread of the cells. Here, the subculture indicates an operation of dissemination of the proliferated cells in culture vessel 121 to another culture vessel, in order to prevent the number of cells in culture vessel 121 from excessively increasing.

As illustrated in FIG. 1, cell culture apparatus 100 includes mounting unit 122, observing unit 110, measurement-position designating unit 111, drive unit 112, image measuring unit 113, image processing unit 114, time-based recording unit 115, and subculture-timing determining unit 116. Culture vessel 121 is mounted on mounting unit 122. Observing unit 110 observes cells in culture vessel 121. Measurement-position designating unit 111 designates one or more measurement positions which are observed by observing unit 110. Drive unit 112 causes observing unit 110 to move to the measurement positions designated by measurement-position designating unit 111. Image measuring unit 113 captures and records observation images at positions designated by measurement-position designating unit 111. Image processing unit 114 calculates a proportion of areas occupied by the cells in the images measured by image measuring unit 113. Time-based recording unit 115 records discrete variations with hour in the confluent rate of the cell calculated by image processing unit 114. Subculture-timing determining unit 116 determines the subculture timing, based on an image processing result at the plurality of positions designated in measurement-position designating unit 111.

Figure 2:
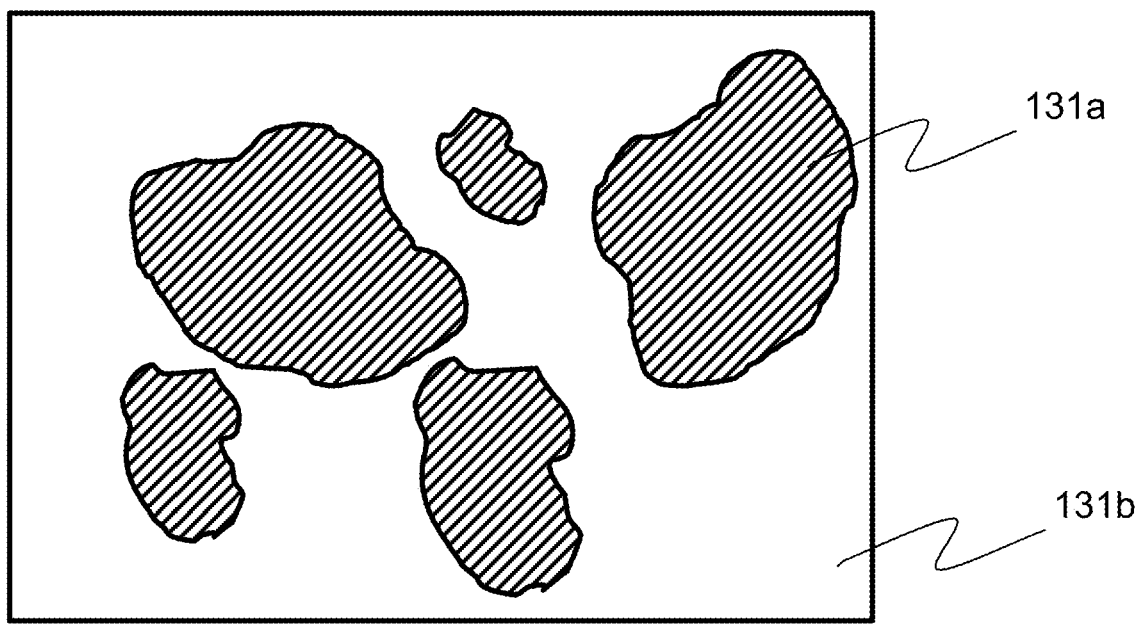
FIG. 2 is a diagram illustrating an observation image of cells according to the exemplary embodiment of the present invention.

Here, the confluent rate of the cells is a proportion of specific areas of the cell portions in the observation image, to the entire area of the observation image. In the specific description with reference to FIG. 2, the entire area of the observation image is an area including hatched region 131a and unhatched region 131b, and the specific area of the cell portions is the area of hatched region 131a.

Subculture-timing determining unit 116 designates a time point at which the subculture is performed, based on average value A of the confluent rate of the cells measured at the plurality of measurement positions designated by measurement-position designating unit 111. Specifically, the confluent rate of the cells is checked by predetermined period of time, the subculture is performed when the average value A of the confluent rate exceeds predetermined first threshold value Ap of the confluent rate. Note that first threshold value Ap is set as the confluent rate at which the cells proliferates at a low speed when the confluent rate exceeds the threshold value, and is set in consideration of the efficiency of the cell culture.

Figure 3:
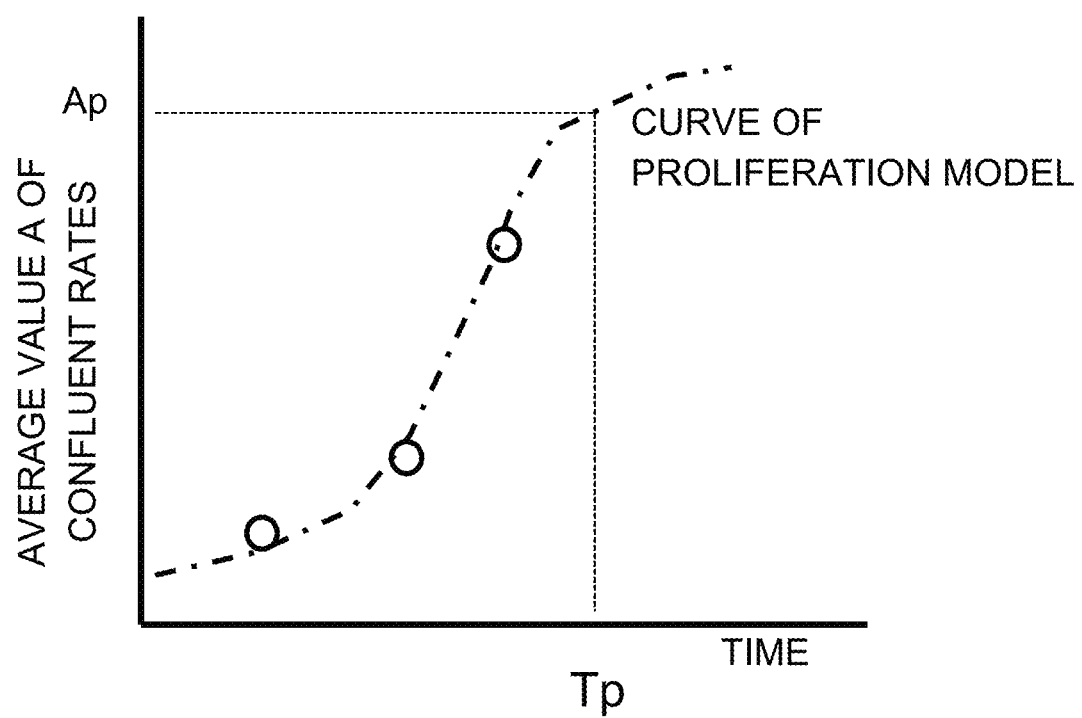
FIG. 3 is a graph illustrating a relationship between a confluent rate and a period of time in the exemplary embodiment of the present invention.

Subculture-timing determining unit 116 determines the subculture timing as illustrated in FIG. 3, in consideration of the uneven spread of the cell proliferation in the observation image in addition to average value A of the confluent rate. In other words, even in a case where average value A of the confluent rate is smaller than first threshold value Ap, the subculture is performed in a case where the confluent rate is locally larger than preset second threshold value Ap' due to the uneven spread of the cells. Here, second threshold value Ap' is a value larger than first threshold value Ap. For example, in a case where human iPS cells are cultured in an undifferentiated state, that an increase in the confluent rate causes the cells to be differentiated is known. The detection of local confluent rate and a corresponding countermeasure prevent the cells from being locally differentiated and thus it is possible to prevent the cells from being degraded. Note that, when second threshold value Ap' exceeds the threshold value, there is a possibility that differentiated cells will be found together in an undifferentiation maintaining culture of the human iPS cells, and thus second threshold value Ap' is set.

A case of uneven spread of the main cells occurs in two types of states including a state in which the disseminated cells unevenly spread in the central portion of culture vessel 121 due to a vortex on a culture medium generated in culture vessel 121 (hereinafter, referred to as a "first uneven-spread state") and a state in which the disseminated cells unevenly spread in a straight line shape in culture vessel 121 due to a wave of the culture medium generated in response to acceleration and deceleration during transportation of culture vessel 121 (hereinafter, referred to as a "second uneven-spread state").

For example, since culture vessel 121 is often caused to move such that a positional relationship between culture vessel 121, a manipulator, and the like changes, after the dissemination of the cells, the first uneven-spread state or the second uneven-spread state described above is likely to occur.

Figure 4A:
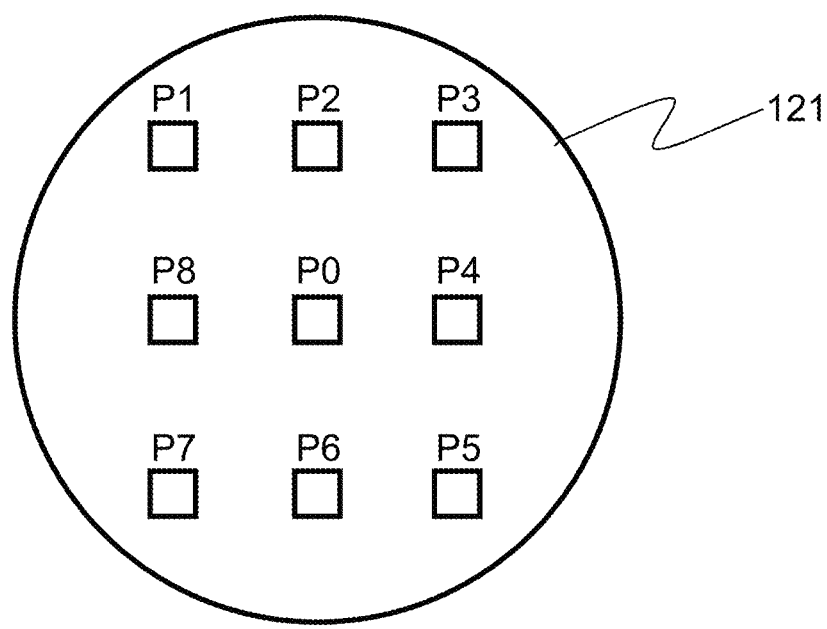
FIG. 4A is a view illustrating measurement positions in the exemplary embodiment of the present invention.

Therefore, measurement-position designating unit 111 needs to set the measurement position such that the two types of phenomena are reliably checked. Specific setting is described with reference to FIGS. 4A and 4B. In the exemplary embodiment, as illustrated in FIG. 4A, a center of culture vessel 121 is set as measurement area P0, and measurement areas P1 to P8 are set at equal intervals along a side of a square at positions separated from measurement area P0 by at least a predetermined distance (2 cm in a petri dish of 10 cm). Specific culture vessel 121 used here is a vessel with a circular bottom having a diameter of 10 cm, and the measurement area is a rectangular region (3 mm×4 mm). In the case of having such setting, in order to check the phenomenon of the first uneven-spread state, at least center P0 of culture vessel 121 is set to measure one area. In addition, in order to check the phenomenon of the second uneven-spread state, P0 in the central portion and any two areas P7 and P5 other than the central portion of culture vessel 121 need to be measured. However, in order to check the phenomenon of the second uneven-spread state, at least one area (for example, in FIG. 4B, measurement area P5), out of the straight line passing measurement area P0 and a measurement area (for example, in FIG. 4B, measurement area P7) other than measurement area P0, need to be measured.

Figure 4B:
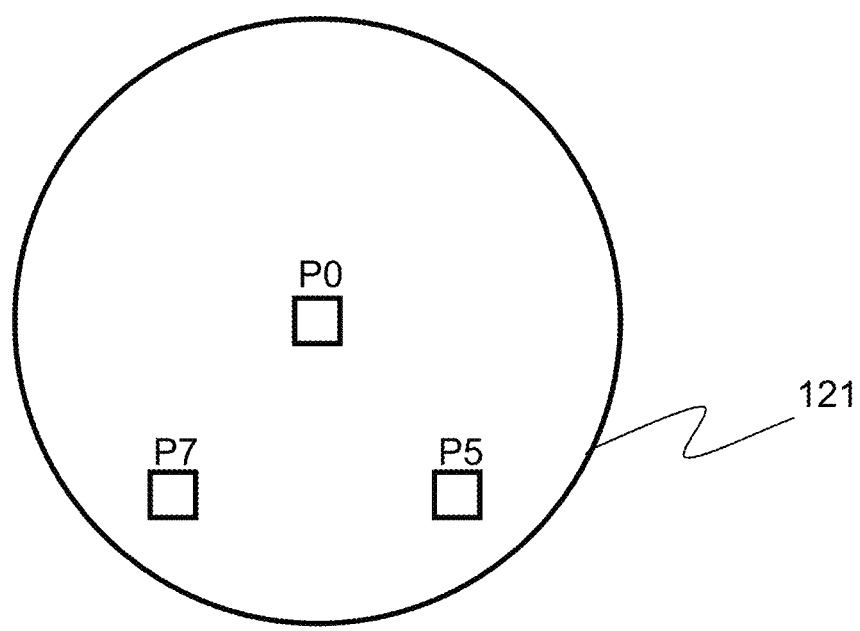
FIG. 4B is a view illustrating examples of measurement positions in the exemplary embodiment of the present invention.

When measurement-position designating unit 111 designates, as the measurement position, at least three areas illustrated in FIG. 4B since the first uneven-spread state and the second uneven-spread state described above do not simultaneously occur, it is possible to find a phenomenon in which the confluent rate locally increases.

Figure 5A:
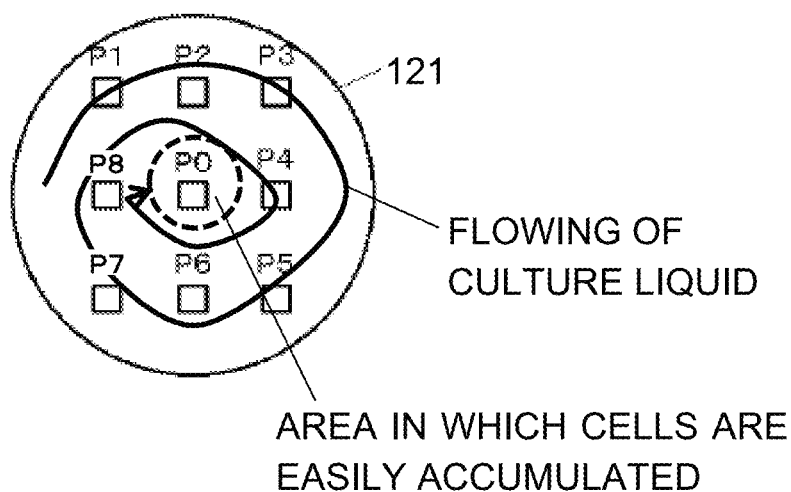
FIG. 5A is a view illustrating a first uneven-spread state in the exemplary embodiment of the present invention.
Figure 5B:
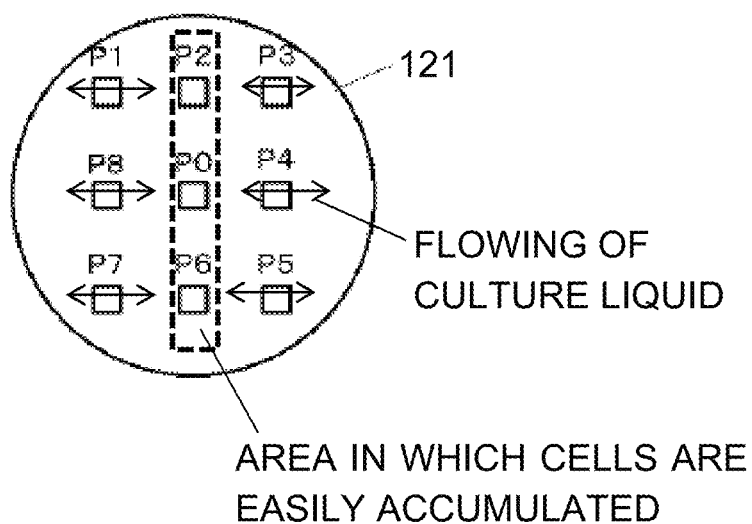
FIG. 5B is a view illustrating a second uneven-spread state in the exemplary embodiment of the present invention.

Here, a phenomenon of the first uneven-spread state and a phenomenon of the second uneven-spread state are specifically described with reference to the figures. FIG. 5A is a diagram illustrating the first uneven-spread state in the exemplary embodiment. FIG. 5B is a diagram illustrating the second uneven-spread state in the exemplary embodiment.

In the first uneven-spread state, in the process of transportation of culture vessel 121, since culture liquids flow to form a vortex shape in culture vessel 121, the cells are likely to be accumulated in measurement area P0 of the center of culture vessel 121. Meanwhile, in the second uneven-spread state, in the process of the transportation of culture vessel 121, since the culture liquids flow in a transverse wave shape in culture vessel 121, the cells are likely to be accumulated to form a straight line shape (here, measurement areas P2, P0, and P6) in culture vessel 121.

Conditions under which the subculture is determined and performed are more described in detail. In a case where the nine areas (P0 to P8) described above are designated as the measurement positions, the subculture starts to be performed in a case where any one of the following three conditions is satisfied.

(1) A case where average value A of the confluent rate in all of the measurement areas of the measurement areas P0 to P8 exceeds first threshold value Ap.

(2) A case where average value A of the confluent rate in all of the measurement areas of measurement areas P0 to P8 is smaller than first threshold value Ap; however, the confluent rate of center P0 exceeds second threshold value Ap'.

(3) A case where average value A of the confluent rate in all of the measurement areas of measurement areas P0 to P8 is smaller than first threshold value Ap; however, the confluent rate of two or more areas (for example, measurement areas P1, P0, and P5, or measurement areas P1, P8, and P7) existing on a straight line shape of measurement areas P0 to P8 exceeds second threshold value Ap'. Here, (2) above is a condition in which the first uneven-spread state described above is determined, and (3) above is a condition in which the second uneven-spread state described above is determined.

Determination of whether or not each condition is satisfied makes it possible to determine the first uneven-spread state or the second uneven-spread state. Specifically, it is also possible that a case where (1) above is not satisfied, but (2) above is satisfied, the first uneven-spread state is determined, and a case where (1) above is not satisfied, but (3) above is satisfied, the second uneven-spread state is determined. Note that, in a case where the conditions of (1) to (3) above are not satisfied, for example, in a case where only two areas (for example, measurement areas P5 and P7) which do not exist on the straight line of measurement areas P1 to P8 exceed the value of the second threshold value Ap', or the like, the variations in a selection method of the measurement area without the uneven spread in the cell proliferation is determined, and thus the subculture is not performed. In a case where human iPS cells are cultured in colonies, and first threshold value Ap is from 45% to 70%, and second threshold value Ap' is from 75% to 90%, it is possible to culture the cells while the cells are maintained in a stable manner without degradation. More preferably, it is possible to culture the cells while the cells are maintained in a more stable manner without degradation, in a case where first threshold value Ap is 60% and second threshold value Ap' is 80%.

Note that, when the values of threshold values Ap and Ap' are set to be low, the cells are maintained to have high qualities; however, the proliferation of the cells decreases and the number of divisions decreases.

Meanwhile, when the values of threshold values Ap and Ap' are set to be high, the qualities of the cells are likely to be degraded; however, it is possible to increase the number of cells so as to increase the number of divisions. In other words, a mode of having an emphasis on quality of the cells in the culture and a mode of having an emphasis on the number of the cells are set, and values of threshold values Ap and Ap' are smaller than normal in a case where the mode of having an emphasis on quality is selected. The values of threshold values Ap and Ap' are larger than normal in a case where the mode of having an emphasis on the number is selected, and thereby it is possible to perform the subculture in which the quality or the number of cells is emphasized.

Note that it is possible to estimate a period of subculture time by calculating an approximate cell growth curve illustrated in FIG. 3 on the basis of a cell proliferation model set depending on types of cells designated in advance and a change in the confluent rate recorded in time-based recording unit 115 and then estimating a time point Tp at which the confluent rate reaches predetermined first threshold value Ap. In this manner, it is possible to perform the subculture at a more appropriate timing, and thus it is possible to realize stability in the quality of the cells.

Note that, in the culture vessel having the confluent rate that exceeds the second threshold value, there is a possibility that the confluent rate will locally increase and degraded cells will be mixed therein. Therefore, the cell culture apparatus is further provided with a culture vessel information control unit that controls information of captured images, date and time of capturing, captured measurement area, and the like of the culture vessel, and that adds a graph to information as data associated with a culture vessel to a culture vessel having the confluent rate exceeding the second threshold value. The graph shows that the confluent rate exceeds the second threshold value. In a case where a user operates the culture vessel, a message indicating that the confluent rate exceeds the second threshold value is displayed on a display unit disposed in the cell culture apparatus, and it is possible to notify the user of the message.

Note that, in a case where the cells proliferate not in a single cell state, but in the colony as the human iPS cells, image processing unit 114 can not only calculate the confluent rate of the cells, but also calculate the diameter of the colony. In the case of the human iPS cells, the cells are known to be differentiated in a case where the colony has a very large diameter. It is preferable that subculture-timing determining unit 116 determines the subculture timing on the basis of the confluent rate and distribution the colonies having diameters in the plurality of measurement positions. In this manner, it is possible to perform culture with high accuracy with quality maintained.

INDUSTRIAL APPLICABILITY

The method of culturing cells of the present invention is applicable to a regenerative medicine and a drug discovery field.

REFERENCE MARKS IN THE DRAWINGS 100 cell culture apparatus
110 observing unit
111 measurement-position designating unit
112 drive unit
113 image measuring unit
114 image processing unit
115 time-based recording unit
116 subculture-timing determining unit
121 culture vessel
122 mounting unit
131a hatched region
131b unhatched region

The invention claimed is:
1. A method of culturing cells comprising:
dividing a culture area into a center area and a plurality of peripheral areas, and designating the center area and the plurality of peripheral areas as measurement positions;
driving an observing unit to the measurement positions;
capturing and recording images at the measurement positions by an image measuring unit coupled to the observing unit;
calculating from the images by an image processing unit:
a confluent rate at each of the measurement positions designated; and
an average confluent rate which is an average of sum of the confluent rates at the measurement positions designated, the confluent rate being defined as a proportion of an area occupied by cells in a designated area; and
determining a timing to perform a subculture of the cells, based on the confluent rate,
wherein the determining of the timing further includes determining when the average confluent rate is smaller than a first threshold value, the confluent rate of the center area is larger than a second threshold value, and the second threshold value is larger than the first threshold value; and
performing the subculture of the cells based on the determined timing.
2. The method of culturing cells according to claim 1,
wherein, in a case where a square whose center is a point included in the center area is defined, the plurality of peripheral areas are eight areas including four vertex points at the square and four middle points of four sides at the square.

3. The method of culturing cells according to claim 2, wherein, the center area and the plurality of peripheral areas are separated from each other.

4. The method of culturing cells according to claim 3, wherein the plurality of peripheral areas are the eight areas whose centers are the four vertex points at the square and the four middle points of the four sides at the square.

5. The method of culturing cells according to claim 1, wherein the first threshold value is from 45% confluent rate to 70% confluent rate, both inclusive, and the second threshold value is from 75% confluent rate to 90% confluent rate, both inclusive.

6. The method of culturing cells according to claim 5, wherein the first threshold value is 60% confluent rate, and the second threshold value is 80% confluent rate.

7. A method of culturing cells using a cell culture apparatus which includes a mounting unit of a culture vessel, an observing unit of a cell in the culture vessel, a measurement-position designating unit, a drive unit, an image measuring unit, an image processing unit and a subculture-timing determining unit, the method comprising:
   dividing a culture area of the culture vessel into a center measurement area and a plurality of peripheral measurement areas by the measurement-position designating unit, the center measurement area having a predetermined region, the plurality of peripheral measurement areas having a predetermined region surrounding the central measurement area and being separated from the central measurement area by at least a predetermined distance, and designating the center measurement area and the plurality of peripheral measurement areas as measurement areas;
   driving the observing unit to the measurement areas by the drive unit;
   capturing and recording images at the measurement areas by the image measuring unit coupled to the observing unit;
   calculating from the images by the image processing unit:
      a confluent rate at each of the measurement areas designated; and
      an average confluent rate which is an average of sum of the confluent rates at the measurement areas designated, the confluent rate being defined as a proportion of an area occupied by cells in a designated area; and
   determining a timing to perform a subculture of the cells by the subculture-timing determining unit, based on the confluent rate, wherein the determining of the timing further includes determining when the average confluent rate is smaller than a first threshold value, the confluent rate of the center area is larger than a second threshold value, and the second threshold value is larger than the first threshold value; and
   performing the subculture of the cells based on the determined timing.

* * * * *